(12) United States Patent
Nesterenko et al.

(10) Patent No.: US 8,450,233 B2
(45) Date of Patent: May 28, 2013

(54) PROCESS FOR OBTAINING CATALYST COMPOSITES COMPRISING MEAPO AND THEIR USE IN CONVERSION OF ORGANICS TO OLEFINS

(75) Inventors: Nikolai Nesterenko, Nivelles (BE); Walter Vermeiren, Houthalen (BE); Sander Van Donk, Sainte-Adresse (FR)

(73) Assignee: Total Petrochemicals Research Feluy, Seneffe (Feluy) (BE)

( * ) Notice: Subject to any disclaimer, the term of this patent is extended or adjusted under 35 U.S.C. 154(b) by 218 days.

(21) Appl. No.: 12/811,218

(22) PCT Filed: Jan. 23, 2009

(86) PCT No.: PCT/EP2009/050756
§ 371 (c)(1),
(2), (4) Date: Dec. 27, 2010

(87) PCT Pub. No.: WO2009/092780
PCT Pub. Date: Jul. 30, 2009

(65) Prior Publication Data
US 2011/0118425 A1 May 19, 2011

(30) Foreign Application Priority Data

Jan. 25, 2008 (EP) .................................. 08150686

(51) Int. Cl.
*B01J 29/06* (2006.01)
*C08F 2/00* (2006.01)
*C07C 1/00* (2006.01)

(52) U.S. Cl.
USPC ................ 502/67; 502/64; 526/75; 585/639; 585/641

(58) Field of Classification Search
USPC ........................................................ 526/133
See application file for complete search history.

(56) References Cited

U.S. PATENT DOCUMENTS 3,855,267 A    12/1974  Cobb
2005/0070422 A1    3/2005  Chen
2005/0075525 A1    4/2005  Chang
2006/0161035 A1 *  7/2006  Kalnes et al. ................ 585/639
2006/0195001 A1 *  8/2006  Coute et al. .................. 585/639

FOREIGN PATENT DOCUMENTS

| EP | 1277 826   | * | 1/2003 |
| EP | 1277826 A  |   | 1/2003 |
| WO | 0205952 A  |   | 1/2002 |

* cited by examiner

Primary Examiner — David W Wu
Assistant Examiner — Elizabeth Eng

(57) ABSTRACT

The present invention relates to a mixture comprising 0.01 to 30% by weight of at least one medium or large pore crystalline silicoaluminate, silicoaluminophosphate materials or silicoaluminate mesoporous molecular sieves (co-catalyst) (A) and respectively 99.99 to 70% by weight of at least a MeAPO molecular sieve. The present invention also relates to catalysts consisting of the above mixture or comprising the above mixture. The present invention also relates to a process (hereunder referred as "XTO process") for making an olefin product from an oxygen-containing, halogenide-containing or sulphur-containing organic feedstock, wherein said oxygen-containing, halogenide-containing or sulphur-containing organic feedstock is contacted with the above catalyst (in the XTO reactor) under conditions effective to convert the oxygen-containing, halogenide-containing or sulphur-containing organic feedstock to olefin products (the XTO reactor effluent). The present invention also relates to a process (hereunder referred as "combined XTO and OCP process") to make light olefins from an oxygen-containing, halogenide-containing or sulphur-containing organic feedstock comprising: contacting said oxygen-containing, halogenide-containing or sulphur-containing organic feedstock in the XTO reactor with the above catalyst at conditions effective to convert at least a portion of the feedstock to form an XTO reactor effluent comprising light olefins and a heavy hydrocarbon fraction; separating said light olefins from said heavy hydrocarbon fraction; and contacting said heavy hydrocarbon fraction in the OCP reactor at conditions effective to convert at least a portion of said heavy hydrocarbon fraction to light olefins.

35 Claims, 1 Drawing Sheet

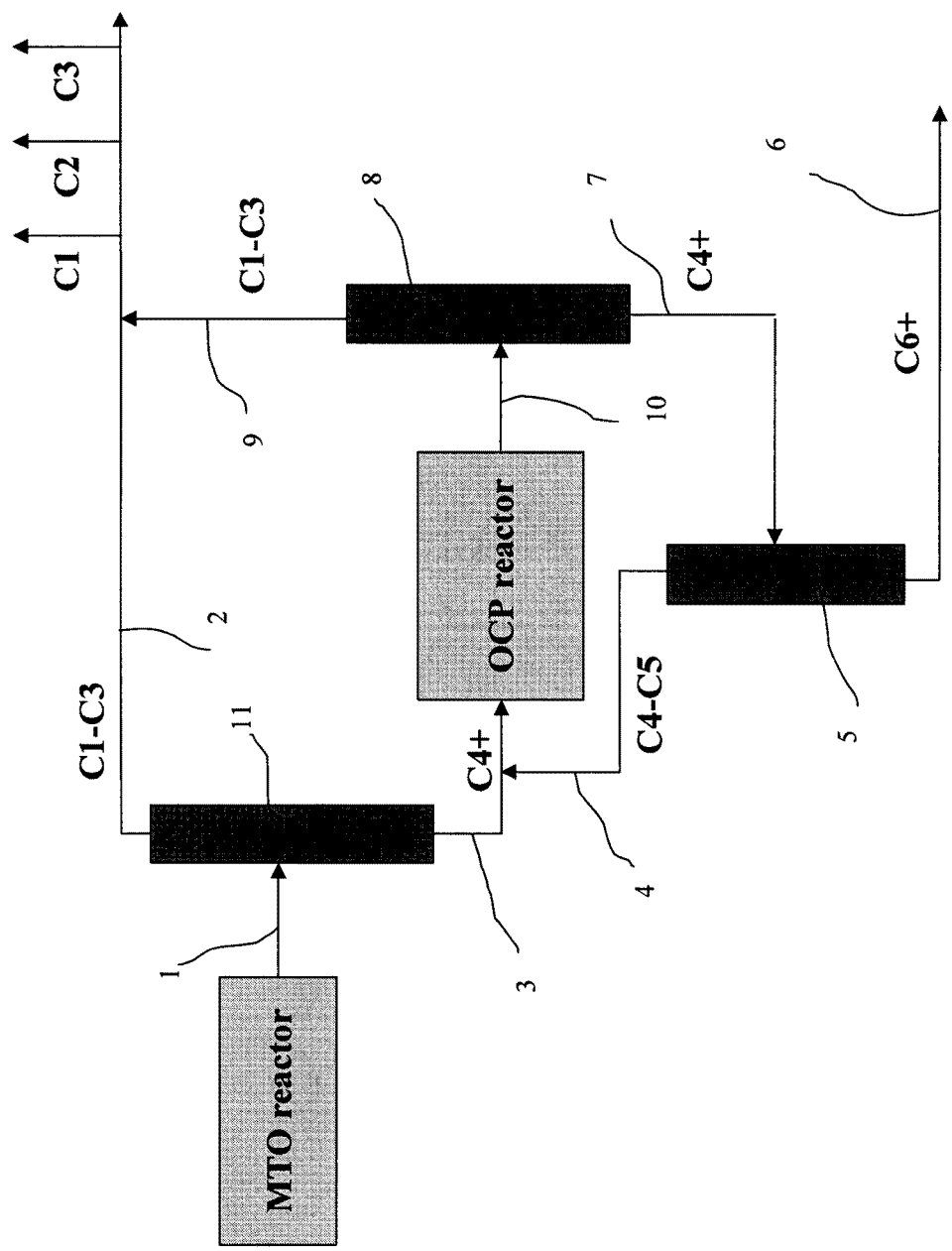

PROCESS FOR OBTAINING CATALYST COMPOSITES COMPRISING MEAPO AND THEIR USE IN CONVERSION OF ORGANICS TO OLEFINS

FIELD OF THE INVENTION

The present invention relates to catalyst composites comprising promoters and mixtures of molecular sieves containing MeAPO, as well as their use in conversion of organics to olefins. More precisely the mixture of molecular sieves comprises MeAPO and a crystalline silicoaluminate or silicate molecular sieve. The crystalline silicoaluminate or silicate molecular sieves have medium to large pore sizes in comparison with the small pore sizes of the MeAPO. The mixtures together with the promoter of the invention provide useful catalyst composites suitable for a variety of processes including cracking, hydrocracking, isomerization, reforming, dewaxing, alkylation, transalkylation and conversion of oxygenates (or halogenide-containing or sulphur-containing organic compounds) to light olefins.

BACKGROUND OF THE INVENTION

The limited supply and increasing cost of crude oil has prompted the search for alternative processes for producing hydrocarbon products. One such process is the conversion of oxygen-containing (by way of example methanol), halogenide-containing or sulphur-containing organic compounds to hydrocarbons and especially light olefins (by light olefins it is meant $C_2$ to $C_4$ olefins) or gasoline and aromatics. In the present application the conversion of said oxygen-containing (also referred to as oxygenates), halogenide-containing or sulphur-containing organic compounds to hydrocarbons and especially light olefins is referred to as the XTO process. The interest in the XTO process is based on the fact that feedstocks, especially methanol can be obtained from coal, biomass, organic waste or natural gas by the production of synthesis gas which is then processed to produce methanol. The XTO process can be combined with an OCP (olefins cracking process) process to increase production of olefins. The XTO process produces light olefins such as ethylene and propylene as well as heavy hydrocarbons such as butenes and above. These heavy hydrocarbons are cracked in an OCP process to give mainly ethylene and propylene.

U.S. Pat. No. 6,951,830B2 relates to a catalyst composition, a method of making the same and its use in the conversion of a feedstock, preferably an oxygenated feedstock, into one or more olefin(s), preferably ethylene and/or propylene. The catalyst composition comprises a molecular sieve, such as a silicoaluminophosphate and/or an aluminophosphate, hydrotalcite, and optionally a rare earth metal component. The rare earth metal compound can be in the form of acetates, halides, oxides, oxyhalides, hydroxides, sulphides, sulphonates, borides, borates, carbonates, nitrates, carboxylates and mixtures thereof.

US20070043250A1 describes an oxygenate conversion catalyst useful in the conversion of oxygenates such as methanol to olefinic products which is improved by the use of a catalyst combination based on a molecular sieve in combination with a co-catalyst comprising a mixed metal oxide composition which has oxidation/reduction functionality under the conditions of the conversion. This metal oxide co-catalyst component will comprise a mixed oxide of one or more, preferably at least two, transition metals, usually of Series 4, 5 or 6 of the Periodic Table, with the metals of Series 4 being preferred, as an essential component of the mixed oxide composition. The preferred transition metals are those of Groups 5, especially titanium and vanadium, Group 6, especially chromium or molybdenum, Group 7, especially manganese and Group 8, especially cobalt or nickel. Other metal oxides may also be present. The preferred molecular sieve components in these catalysts are the high silica zeolites and the silicoaluminophosphates (SAPOs), especially the small pore SAPOs (8-membered rings), such as SAPO-34. These catalyst combinations exhibiting reduced coke selectivity have the potential of achieving extended catalyst life. In addition, these catalysts have the capability of selectively converting the hydrogen produced during the conversion to liquid products, mainly water, reducing the demand on reactor volume and product handling.

U.S. Pat. No. 7,186,875 discloses a process for converting an oxygenate-containing feedstock into one or more olefins in a reactor system including a plurality of fixed bed reactors each containing a catalyst composition comprising a molecular sieve and at least one metal oxide having an uptake of carbon dioxide at 100° C. of at least 0.03 mg/m$^2$ of the metal oxide. Each reactor is sequentially rotated between at least one operating mode, wherein the catalyst composition in the reactor is contacted with the oxygenate-containing feedstock, and a regeneration mode, wherein the catalyst composition in the reactor is contacted with a regeneration medium. The molecular sieve is a silicoaluminophosphate (SAPO) and/or a metal substituted SAPO. The metal oxide used in the composition, it is stated, is different from typically used binders and/or matrix material, in that it extends the life of the catalyst composition. Suitable metal oxides include those metal oxides having a Group 2, Group 3 (including the Lanthanides and Actinides) or Group 4 metal. There is no mention of any metal salts.

US 2003/0176752 describes a catalyst composition, a method making the same and its use in the conversion of a feedstock, preferably an oxygenated feedstock, into one or more olefin(s), preferably ethylene and/or propylene. The catalyst composition comprises a molecular sieve and at least one oxide of a metal from Group 4, optionally in combination with at least one metal from Groups 2 and 3. The metal oxide has an uptake of carbon dioxide at 100° C. of at least 0.03 mg/m$^3$. The molecular sieve is preferably a silicoaluminophosphate and/or metal derivatives thereof.

US 2004/0030213 discloses describes an oxygenate conversion catalyst based a combination of a molecular sieve such as SAPO-34 and an oxide of a metal of Group 3, including the lanthanide series and the actinide series. Examples of such oxides include lanthanum oxide, yttrium oxide, scandium oxide, cerium oxide, praseodymium oxide, neodymium oxide, samarium oxide and thorium oxide.

This catalytic combination is reported to result in similar advantages when used in methanol conversion reactions and, in addition, results in a reduction in the amounts of undesirable by-products such as aldehydes and ketones, especially acetaldehyde. In addition, it is claimed that the catalyst compositions are less susceptible to coke formation and thus have longer lifetimes. It is also stated that the higher density of these catalyst compositions is believed to improve operability in the overall conversion process. The denser catalyst particles are retained to a greater extent within the unit, whether in the reactor or its associated regenerator, resulting in lower catalyst losses.

WO 1998029370 discloses the conversion of oxygenates to olefins over a small pore (less than 5 nm) non-zeolitic molecular sieve containing an oxide of a lanthanide metal or an actinide metal, scandium, yttrium, a Group 4 metal, a Group 5 metal or combinations thereof. The metal-containing compound is introduced to the non-zeolitic molecular sieve in the form of the corresponding halide, sulphate, acetate, formate, propionate, oxalate, maleate, fumarate, carboxylate, alkoxide, carbonyl, nitrate or mixtures thereof. These small pore molecular sieve compositions are claimed to be more stable even at high conversion rates. These salts however are oxide-precursor salts and thus not stable at the high temperature conditions of the MTO process. Furthermore, selectivity to propylene is markedly low.

Molecular sieves in combination with matrix and binder components for XTO processes are known in the art. Usually, the binder and matrix are chemically neutral materials, typically serving only to provide desired physical characteristics to the catalyst composition. Usually, they have very little effect on catalytic performance. These molecular sieve catalyst compositions are formed by combining the molecular sieve and the matrix e.g. an inorganic oxide such as alumina, titania, zirconia, silica or silica-alumina with a binder, e.g. clay, to form a cohesive, mechanically stable, attrition-resistant composite of the sieve, matrix material and binder. In particular, the use of silica ($SiO_2$) as a binder/matrix material is well known in the art. This solid is neutral and is selected when catalytic effects of the binder/matrix are undesired. Typically, rare earth elements, which are very expensive, are used in such catalyst composites.

Metal is introduced typically in the form of oxides/oxide-precursor salts by ion-exchange or impregnation. However, ion-exchange/impregnation potentially leads to the modification of the acidity of catalytic sites throughout the whole microporous structure of the molecular sieve. This could lead to decreased catalytic activity. Metal oxides are chemically active compounds. Without taking special precautions during pre-treatment and catalyst formulation these compounds may partially damage the molecular sieve pore structure. The proposed present invention is very different from the prior art. It avoids the use of metal oxides or unstable oxide-precursor salts. The combination of molecular sieves with chemically inert metal salts which are stable under the conversion process of the oxygenates to the olefins, allows selectively modifying only the sites located on the external surface and in the pore mouths of the molecular sieve. As a result, the formation of side products is minimised and coke formation is decreased without losses in the catalyst's activity.

Small pore silicoaluminophosphate (SAPO) molecular sieve catalysts have excellent selectivity in oxygenates to light olefin reactions. However, these catalysts have a tendency to deactivate rapidly during the conversion of oxygenates to olefins and the ratio C3/C2 could be improved. Therefore a need exists for methods to decrease the rate of deactivation of small pore molecular sieve catalysts during such conversions and to improve the yield of light olefins and the C3/C2 ratio.

It has been discovered that addition of a small amount of metal salts to a small pore MeAPO molecular sieve or optionally to a composite molecular sieve containing a combination of small pore MeAPO molecular sieve with medium or large pore crystalline silicoaluminate, silicoaluminophosphate materials or silicoaluminate mesoporous molecular sieves leads to substantial increase of C3/C2 ratio, yield of light olefins and stability in XTO than was obtained over the parent molecular sieve alone (MeAPO).

Higher stability of the blended catalysts together with the metal salt provides a possibility to operate at higher flow rate, increase the catalyst on-stream time in XTO conversion reactor and decrease the size of regeneration section or the frequency of regeneration. (on-stream time is the time that a catalyst resides in the conversion reactor and exhibits still sufficient catalytic activity, before it has to be taken off-line for regeneration or replacement)

Unexpectedly, this catalyst composite possesses reduced coke selectivity in comparison with the weighted average of the individual molecular sieves.

The excess of C4+ as well as ethylene can be converted to propylene in an olefin cracking fixed bed reactor (OCP) in combination with the XTO process. Ethylene can be recycled back in XTO reactor or to the OCP reactor. The excess C4+ as well as the ethylene can be converted to more propylene by recycling C4+ and ethylene back to the XTO reactor. The catalyst blend allows the conversion of organic compounds, C4+ and ethylene at the same time.

Stated above, small pore MeAPO molecular sieves contain 8-membered rings as the largest pore aperture in the structure, medium pore crystalline silicoaluminates contain 10-membered rings as the largest pore aperture; large pore crystalline silicoaluminates contain 12-membered rings as the largest pore aperture. Stated above medium, large pore and mesoporous molecular sieves have acidic properties, which are capable in catalysing the formation of aromatic precursors from used feedstock.

In the XTO process the ethylene, propylene and higher hydrocarbons are formed via a "carbon pool" mechanism (Dahl and Kolboe 1994 *Journal of Catalysis* 149(2): 458-464; Dahl and Kolboe 1996 *Journal of Catalysis* 161(1): 304-309; Stocker 1999, *Microporous and Mesoporous Materials* 29(1-2): 3-48). Ethylene, propylene and C4+ olefins selectivities in XTO process are related to the number of methyl groups attached to benzene rings trapped in the nanocages. The product spectrum varies strongly with the pore size of the catalytic material (shape selectivity), and when the small pore SAPO-34 (chabasite structure) is used as catalyst the hydrocarbon products are mostly ethene and propene, and some substantially linear butenes, the only product molecules small enough to escape with ease through the narrow pores.

It has been discovered that medium or large pore crystalline silicoaluminate, silicoaluminophosphate materials or silicoaluminate mesoporous molecular sieves play a role of a faster in-situ supply for aromatic precursors for olefin production by the carbon pool mechanism. One optional aspect of this invention is in-situ on-purpose formation of some additional organic reaction centers by adding to the MeAPO a small amount of acid co-catalyst with larger pore opening than the MeAPO. These materials are capable to produce a small amount of higher molecular weight precursors that can enter into the pore system of the small pore MeAPO where they are converted into the aromatics under XTO conditions. These aromatics constitute the active centers for XTO according to the carbon pool mechanism. These aromatics are trapped by MeAPO micro porous system in a more optimum way without formation of a lot of coke by-products. This allows an increased catalyst stability and C3/C2 ratio.

Without being bonded by any theory, inventors think that an optimum concentration of the methylbenzenes organic reaction centers leads to higher light olefins production and to a slower deactivation. However the olefin production is limited by diffusion of heavy olefins out of the micropore system of MeAPO in which usually methylbenzenes are trapped. Formation of the methylbenzenes inside of MeAPO pore system requires a certain time and is accompanied by coke formation. More coke formation in the small pore MeAPO reduces the accessible pore volume and results in faster loss of catalytic activity.

BRIEF SUMMARY OF THE INVENTION

The invention covers a catalyst composite comprising:
at least 0.5% by weight of at least one metal salt stable under XTO conditions and
at least 10% by weight of molecular sieve, which comprises:
- 70 to 100% by weight of at least one small pore aluminosilicate or metalloaluminophosphate (MeAPO) molecular sieve selected from the group CHA, AEI, ERI, LEV or a mixture of thereof and
- 0 to 30% by weight of at least one medium or large pore molecular sieve selected from one or more of crystalline silicoaluminates, silicoaluminophosphates or mesoporous silicoaluminates.

Preferably, the composite comprises from 0.5 to 10% by weight of at least one metal salt, more preferably from 1 to 10%. The metal salt may comprise at least one metal from the following: Zn, Co, Ca, Mg, Ga, Al, Cs, Sr, Ba, Sc, Sn and Li. Preferably, the metal is Zn, Co, Ca, Mg. At least one of the anions of the metal salt is advantageously selected from silicates, borates and borosilicates.

Advantageously, the molecular sieves comprise 70 to 99.9% by weight of the MeAPO molecular sieve and 0.01 to 30% by weight of the medium or large pore molecular sieve. More advantageously, the molecular sieves comprise 75 to 99.5% by weight of the MeAPO molecular sieve and 0.5 to 25% by weight of the medium or large pore molecular sieve. Most advantageously, the molecular sieves comprise 85 to 99% by weight of the MeAPO molecular sieve and 1 to 15% by weight of the medium or large pore molecular sieve.

MFI, FER and MEL are the most preferable medium pore crystalline silicoaluminates.

AEL is the most preferable medium pore silicoaluminophosphate material.

FAU, MOR, LTL, MAZ, MWW and BEA are the most preferable large pore crystalline silicoaluminates.

AFI is the most preferable large pore silicoaluminophosphate materials,

MCM-41, SBA-15, SBA-16 are the most preferable mesoporous molecular sieve.

MeAPO's have a three-dimensional microporous crystal framework of $PO_2^+$, $AlO_2^-$, and $MeO_2$ tetrahedral units. MeAPO molecular sieves having CHA (SAPO-34, SAPO-44), LEV (SAPO-35), ERI (SAPO-17) or AEI (SAPO-18) structure or mixture thereof are the most preferable. Silicon is the most desirable metal in MeAPO.

According to another embodiment of the invention the MeAPO molecular sieve has an empirical chemical composition on an anhydrous basis, after synthesis and calcination, expressed by the formula $H_xMe_yAl_zP_kO_2$ in which, $y+z+k=1$ $x<=y$ y has a value ranging from 0.0008 to 0.4 and advantageously from 0.005 to 0.18 z has a value ranging from 0.25 to 0.67 and advantageously from 0.38 to 0.55 k has a value ranging from 0.2 to 0.67 and advantageously from 0.36 to 0.54

Advantageously said molecular sieve have predominantly plate crystal morphology. Preferably said plate crystal morphology is such as the width (W) and the thickness (T) are as follows:

W/T is >=10 and advantageously ranges from 10 to 100.

According to another embodiment of the invention the MeAPO has been prepared by a method comprising:
a) forming a reaction mixture containing a texture influencing agent (TIA), an organic templating agent (TEMP), at least a reactive inorganic source of $MeO_2$ essentially insoluble in the TIA, reactive sources of $Al_2O_3$ and $P_2O_5$,
b) crystallizing the above reaction mixture thus formed until crystals of the metalloaluminophosphate are formed,
c) recovering a solid reaction product,
d) washing it with water to remove the TIA and
e) calcinating it to remove the organic template.

The catalyst composite can be obtained by introducing the metal salt to the molecular sieve(s) by one of the following two methods:

During the formulation step of the catalyst by mechanically blending the molecular sieve with the metal silicate forming a precursor;

Physical blending of the previously formulated molecular sieve and the previously formulated metal silicate in situ in the XTO and/or OCP reaction medium.

The present invention also relates to a process (hereunder referred as "XTO process") for making an olefin product from an oxygen-containing, halogenide-containing or sulphur-containing organic feedstock wherein said oxygen-containing, halogenide-containing or sulphur-containing organic feedstock is contacted with the above catalyst composite (in the XTO reactor) under conditions effective to convert at least a portion of the oxygen-containing, halogenide-containing or sulphur-containing organic feedstock to olefin products (the XTO reactor effluent). It is desirable to have a substantially 100% conversion of the organic compound in the XTO reactor. This conversion rate is adjusted by optimization of the contact time and the frequency of regeneration of the catalyst composite.

According to a specific embodiment the XTO reactor effluent comprising light olefins and a heavy hydrocarbon fraction is sent to a fractionation section to separate said light olefins from said heavy hydrocarbon fraction; said heavy hydrocarbon fraction is recycled in the XTO reactor at conditions effective to convert at least a portion of said heavy hydrocarbon fraction to olefin products.

With regards to said effluent of the XTO process, "light olefins" means ethylene and propylene and the "heavy hydrocarbon fraction" is defined herein as the fraction containing hydrocarbons having a molecular weight greater than propane, which means hydrocarbons having 4 carbon atoms or more and written as $C_4^+$.

According to another embodiment of the invention said olefin products (the effluent of the XTO) are fractionated to form a stream comprising essentially ethylene and at least a part of said stream is recycled in the XTO reactor to increase the propylene production and then the flexibility of ethylene vs propylene production.

According to another embodiment of the invention both ethylene and the C4+ can be recycled in the XTO reactor.

The present invention also relates to a process (hereunder referred as "combined XTO and OCP process") to make light olefins from an oxygen-containing, halogenide-containing or sulphur-containing organic feedstock comprising:
contacting said oxygen-containing, halogenide-containing or sulphur-containing organic feedstock in the XTO reactor with the above catalyst composite at conditions effective to convert at least a portion of the feedstock to form an XTO reactor effluent comprising light olefins and a heavy hydrocarbon fraction;
separating said light olefins from said heavy hydrocarbon fraction;

contacting said heavy hydrocarbon fraction in the OCP reactor at conditions effective to convert at least a portion of said heavy hydrocarbon fraction to light olefins. It is desirable to have a substantially 100% conversion of the organic compound in the XTO reactor. This conversion rate is adjusted by optimization of the contact time and the frequency of regeneration of the catalyst.

DETAILED DESCRIPTION OF THE INVENTION

Regarding the small pore aluminosilicate and the small pore metalloaluminophosphate (MeAPO), they are known per se. MeAPO are described in U.S. Pat. No. 4,440,871, U.S. Pat. No. 6,207,872, U.S. Pat. No. 6,540,970 and U.S. Pat. No. 6,303,534, the content of which are enclosed in the present application. Preferably they have essentially the structure SAPO-18 (AEI), SAPO-17(ERI), SAPO-35(LEV), SAPO-34 (CHA) or SAPO-44 (CHA) or a mixture thereof. In an advantageous embodiment the MeAPO molecular sieves have essentially a structure CHA or AEI or a mixture thereof.

"Small pore" means typically having pore apertures defined by ring sizes of no more than 8 tetrahedric atoms, preferably ring sizes of 4, 6 or 8 tetrahedric atoms. Preferably, the average pore size is less than about 0.5 nm.

About "essentially" referring to the CHA or AEI structure it means that advantageously more than 80% by weight, preferably more than 90%, of the MeAPO has the structure CHA or AEI or a mixture thereof. About "essentially" referring to the SAPO-18, SAPO-34, SAPO-17, SAPO-35 and SAPO-44 structure, it means that advantageously more than 80% by weight, preferably more than 90%, of the MeAPO has the structure SAPO-18, SAPO-34, SAPO-44, SAPO-17, SAPO-35 or a mixture thereof.

Me is advantageously a metal selected from the group consisting of silicon, germanium, magnesium, zinc, iron, cobalt, nickel, manganese, chromium and mixtures thereof. Preferred metals are silicon, magnesium and cobalt with silicon or germanium being especially preferred.

The MeAPO could be also an intergrown phase of two MeAPO having AEI and CHA framework types. They are described in U.S. Pat. No. 7,067,095, U.S. Pat. No. 6,953,767 and U.S. Pat. No. 6,334,994, the content of which are enclosed in the present application.

Before introduction of the metal salt promoter, other metals such as Si, Co, Zn, Ge, Mg, Ca, Ba, Ni, Mo, Cr, Cu, Fe, Ga, Mn, Sn, Ti may be introduced.

Regarding the MeAPO according to another embodiment of the invention, the MeAPO molecular sieve has an empirical chemical composition on an anhydrous basis, after synthesis and calcination, expressed by the formula $H_xMe_yAl_zP_kO_2$ in which, $y+z+k=1$ $x<=y$ y has a value ranging from 0.0008 to 0.4 and advantageously from 0.005 to 0.18 z has a value ranging from 0.25 to 0.67 and advantageously from 0.38 to 0.55 k has a value ranging from 0.2 to 0.67 and advantageously from 0.36 to 0.54

In an advantageous embodiment y has a value ranging from 0.005 to 0.18, z has a value ranging from 0.38 to 0.55 and k has a value ranging from 0.36 to 0.54.

In a first preferred embodiment y has a value ranging from 0.005 to 0.16, z has a value ranging from 0.39 to 0.55 and k has a value ranging from 0.37 to 0.54.

In a second preferred embodiment y has a value ranging from 0.011 to 0.16, z has a value ranging from 0.39 to 0.55 and k has a value ranging from 0.37 to 0.54.

In a third preferred embodiment y has a value ranging from 0.011 to 0.14, z has a value ranging from 0.40 to 0.55 and k has a value ranging from 0.38 to 0.54.

In an advantageous embodiment the MeAPO molecular sieves have essentially a structure CHA or AEI or a mixture thereof. Preferably they have essentially the structure SAPO 18 or SAPO 34 or a mixture thereof.

Advantageously said molecular sieve have predominantly a plate crystal morphology. Preferably said plate crystal morphology is such that the width (W) and the thickness (T) are as follows:

W/T is >=10 and advantageously ranges from 10 to 100.

In a preferred embodiment T is <=0.15 μm, more desirably <=0.10 μm, more desirably <=0.08 μm, advantageously ranges from 0.01 to 0.07 μm and preferably from 0.04 to 0.07 μm.

About the plate crystal morphology, said plates have advantageously the shape of a simple polygon comprised in a square. The square's length is named W. The MeAPO molecular sieves have predominantly a plate crystal morphology. By predominantly is meant advantageously greater than 50% of the crystals. Preferably at least 70% of the crystals have a plate morphology and most preferably at least 90% of the crystals have a plate morphology. About "essentially" referring to the CHA or AEI structure it means that advantageously more than 80% by weight, preferably more than 90%, of the MeAPO of the invention has the structure CHA or AEI or a mixture thereof. About "essentially" referring to the SAPO-18, SAPO-34 and SAPO-44 structure it means that advantageously more than 80% by weight, preferably more than 90%, of the MeAPO has the structure SAPO 18 or SAPO 34 or a mixture thereof.

With regards to a method to make said MeAPO, it can be made by a method which comprises:

a) forming a reaction mixture containing a texture influencing agent (TIA), an organic templating agent (TEMP), at least a reactive inorganic source of $MeO_2$ essentially insoluble in the TIA, reactive sources of $Al_2O_3$ and $P_2O_5$, said reaction mixture having a composition expressed in terms of molar oxide ratios of:

TEMP/$Al_2O_3$=0.3-5, more desirable 0.5-2

$MeO_2$/$Al_2O_3$=0.005-2.0, more desirable 0.022-0.8

$P_2O_5$/$Al_2O_3$=0.5-2, more desirable 0.8-1.2

TIA/$Al_2O_3$=3-30, more desirable 6-20 b) crystallizing the above reaction mixture thus formed until crystals of the metalloaluminophosphate are formed, c) recovering a solid reaction product, d) washing it with water to remove the TIA and e) calcinating it to remove the organic template.

In an advantageous embodiment TEMP/$Al_2O_3$=0.5-2; $MeO_2$/$Al_2O_3$=0.022-0.8; $P_2O_5$/$Al_2O_3$=0.8-1.2 and TIA/$Al_2O_3$=6-20.

In a first preferred embodiment TEMP/$Al_2O_3$=0.5-2; $MeO_2$/$Al_2O_3$=0.022-0.7; $P_2O_5$/$Al_2O_3$=0.8-1.2 and TIA/$Al_2O_3$=6-20.

In a second preferred embodiment TEMP/$Al_2O_3$=0.7-2; $MeO_2$/$Al_2O_3$=0.05-0.7; $P_2O_5$/$Al_2O_3$=0.8-1.2 and TIA/$Al_2O_3$=6-20.

In a third preferred embodiment TEMP/$Al_2O_3$=0.7-2; $MeO_2$/$Al_2O_3$=0.05-0.6; $P_2O_5$/$Al_2O_3$=0.8-1.2 and TIA/$Al_2O_3$=6-20.

With regards to the TIA, mention may be made, by way of example, of 1,2-propanediol, 1,3-propanediol, methanol, ethanol, propanol, isopropanol, butanol, glycerol or ethylene glycol.

With regards to the organic templating agent, it can be any of those heretofore proposed for use in the synthesis of conventional zeolitic aluminosilicates and microporous aluminophosphates. In general these compounds contain elements of Group VA of the Periodic Table of Elements, particularly nitrogen, phosphorus, arsenic and antimony, preferably N or P and most preferably N, which compounds also contain at least one alkyl or aryl group having from 1 to 8 carbon atoms. Particularly preferred nitrogen-containing compounds for use as templating agents are the amines and quaternary ammonium compounds, the latter being represented generally by the formula $R_4N^+$ wherein each R is an alkyl or aryl group containing from 1 to 8 carbon atoms. Polymeric quaternary ammonium salts such as $[(C_{14}H_{32}N_2)(OH)_2]_x$ wherein "x" has a value of at least 2 are also suitably employed. Both mono-, di and tri-amines are advantageously utilized, either alone or in combination with a quaternary ammonium compound or other templating compound. Representative templating agents include tetramethylammonium, tetraethylammonium, tetrapropylammonium or tetrabutylammonium cations; di-n-propylamine, tripropylamine, triethylamine; diethylamine, triethanolamine; piperidine; morpholine; cyclohexylamine; 2-methylpyridine; N,N-dimethylbenzylamine; N,N-diethylethanolamine; dicyclohexylamine; N,N-dimethylethanolamine; choline; N,N'-dimethylpiperazine; 1,4-diazabicyclo(2,2,2) octane; N-methyldiethanolamine, N-methylethanolamine; N-methylpiperidine; 3-methylpiperidine; N-methylcyclohexylamine; 3-methylpyridine; 4-methylpyridine; quinuclidine; N,N'-dimethyl-1,4-diazabicyclo(2,2,2)octane ion; di-n-butylamine, neopentylamine; di-n-pentylamine; isopropylamine; t-butylamine; ethylenediamine; pyrrolidine; and 2-imidazolidone. Advantageously organic templating agent is selected among tetraethylammonium hydroxide (TEAOH), diisopropylethylamine (DPEA), tetraethyl ammonium salts, cyclopentylamine, aminomethyl cyclohexane, piperidine, triethylamine, diethylamine, cyclohexylamine, triethyl hydroxyethylamine, morpholine, dipropylamine, pyridine, isopropylamine di-n-propylamine, tetra-n-butylammonium hydroxide, diisopropylamine, di-n-propylamine, n-butylethylamine, di-n-butylamine, and di-n-penty-lamine and combinations thereof. Preferably the template, is a tetraethyl ammonium compound selected from the group of tetraethyl ammonium hydroxide (TEAOH), tetraethyl ammonium phosphate, tetraethyl ammonium fluoride, tetraethyl ammonium bromide, tetraethyl ammonium chloride, tetraethyl ammonium acetate. Most preferably, the template is tetraethyl ammonium hydroxide.

With regards to the reactive inorganic source of $MeO_2$ essentially insoluble in the TIA and relating to silicon, non-limiting examples of useful inorganic silicon source materials non-soluble in alcohols include, fumed silica, aerosol, pyrogenic silica, precipitated silica and silica gel.

With regards to the reactive sources of $Al_2O_3$, it can be any aluminum species capable of being dispersed or dissolved in an aqueous synthesis solution. Useful sources of alumina are one or more sources selected from the group consisting of the following: hydrated alumina, organo alumina, in particularly $Al(OiPr)_3$, pseudo-boehmite, aluminum hydroxide, colloidal alumina, aluminium halides, aluminium carboxylates, aluminium sulfates and mixtures thereof.

With regards to the reactive sources of $P_2O_5$, it can be one or more sources selected from the group consisting of phosphoric acid; organic phosphates, such as triethyl phosphate, tetraethyl-ammonium phosphate; aluminophosphates; and mixtures thereof. The phosphorous source should also be capable of being dispersed or dissolved in an alcohol synthesis solution.

These MeAPO can be prepared by the usual methods of the molecular sieves synthesis technology provided it is in accordance with the above-cited ratios. The reaction mixture is in the form of a gel. The ratios $MeO_2/Al_2O_3$ and $P_2O_5/Al_2O_3$ are selected among the above described advantageous and preferred ratios and are in accordance with the advantageous and preferred y, z and k described above. By way of example to make a MeAPO having the y, z and k according to the second preferred embodiment one has to use the ratios of the ingredients according to the second preferred embodiment of the method to make said MeAPO.

With regards to the step b), the reaction mixture obtained by mixing the reactive sources of alumina, $MeO_2$, phosphorus, organic templating agent and TIA is submitted to autogenous pressure and elevated temperature. The reaction mixture is heated up to the crystallization temperature that may range from about 120° C. to 250° C., preferably from 130° C. to 225° C., most preferably from 150° C. to 200° C. Heating up to the crystallization temperature is typically carried out for a period of time ranging from about 0.5 to about 16 hours, preferably from about 1 to 12 hours, most preferably from about 2 to 9 hours. The temperature may be increased stepwise or continuously. However, continuous heating is preferred. The reaction mixture may be kept static or agitated by means of tumbling or stirring the reaction vessel during hydrothermal treatment. Preferably, the reaction mixture is tumbled or stirred, most preferably stirred. The temperature is then maintained at the crystallization temperature for a period of time ranging from 2 to 200 hours. Heat and agitation is applied for a period of time effective to form crystalline product. In a specific embodiment, the reaction mixture is kept at the crystallization temperature for a period of from 16 to 96 hours.

With regards to the step c), the usual means can be used. Typically, the crystalline molecular sieve product is formed as a slurry and can be recovered by standard means, such as by sedimentation, centrifugation or filtration.

With regards to the step d), the separated molecular sieve product is washed, recovered by sedimentation, centrifugation or filtration and dried.

With regards to the step e), calcination of molecular sieves is known per se. As a result of the molecular sieve crystallization process, the recovered molecular sieve contains within its pores at least a portion of the template used. In a preferred embodiment, activation is performed in such a manner that the template is removed from the molecular sieve, leaving active catalytic sites with the microporous channels of the molecular sieve open for contact with a feedstock. The activation process is typically accomplished by calcining, or essentially heating the molecular sieve comprising the template at a temperature of from 200 to 800° C. in the presence of an oxygen-containing gas. In some cases, it may be desirable to heat the molecular sieve in an environment having a low oxygen concentration. This type of process can be used for partial or complete removal of the template from the intracrystalline pore system.

Additionally, if during the synthesis alkaline or alkaline earth metals have been used, the molecular sieve might be subjected to an ion-exchange step. Conventionally, ion-exchange is done in aqueous solutions using ammonium salts or inorganic acids.

Regarding the MeAPO according to another embodiment of the invention the MeAPO has been prepared by a method comprising:

a) forming a reaction mixture containing a texture influencing agent (TIA), an organic templating agent (TEMP), at least a reactive inorganic source of $MeO_2$ essentially insoluble in the TIA, reactive sources of $Al_2O_3$ and $P_2O_5$,
b) crystallizing the above reaction mixture thus formed until crystals of the metalloaluminophosphate are formed,
c) recovering a solid reaction product,
d) washing it with water to remove the TIA and
e) calcinating it to remove the organic template.

In a usual embodiment said reaction mixture has a composition expressed in terms of molar oxide ratios of:
TEMP/$Al_2O_3$=0.3-5, more desirable 0.5-2
$MeO_2$/$Al_2O_3$=0.005-2.0, more desirable 0.022-0.8
$P_2O_5$/$Al_2O_3$=0.5-2, more desirable 0.8-1.2
TIA/$Al_2O_3$=3-30, more desirable 6-20

In an advantageous embodiment TEMP/$Al_2O_3$=0.5-2; $MeO_2$/$Al_2O_3$=0.022-0.8; $P_2O_5$/$Al_2O_3$=0.8-1.2 and TIA/$Al_2O_3$=6-20.

In a first preferred embodiment TEMP/$Al_2O_3$=0.5-2; $MeO_2$/$Al_2O_3$=0.022-0.7; $P_2O_5$/$Al_2O_3$=0.8-1.2 and TIA/$Al_2O_3$=6-20.

In a second preferred embodiment TEMP/$Al_2O_3$=0.7-2; $MeO_2$/$Al_2O_3$=0.05-0.7; $P_2O_5$/$Al_2O_3$=0.8-1.2 and TIA/$Al_2O_3$=6-20.

In a third preferred embodiment TEMP/$Al_2O_3$=0.7-2; $MeO_2$/$Al_2O_3$=0.05-0.6; $P_2O_5$/$Al_2O_3$=0.8-1.2 and TIA/$Al_2O_3$=6-20.

In a usual embodiment the metalloaluminophosphate (MeAPO) molecular sieves made with the above method have a lamellar crystal morphology having an empirical chemical composition on an anhydrous basis, after synthesis and calcination, expressed by the formula $H_xMe_yAl_zP_kO_2$ wherein,
y+z+k=1
x<=y
y has a value ranging from 0.0008 to 0.4 and more desirable from 0.005 to 0.18
z has a value ranging from 0.25 to 0.67 and more desirable from 0.38 to 0.55
k has a value ranging from 0.2 to 0.67 and more desirable from 0.36 to 0.54
said molecular sieve having predominantly a plate crystal morphology.

The values of y, z and k in the usual embodiment are obtained by the ratios of the ingredients described in the usual embodiment method above described.

In an advantageous embodiment y has a value ranging from 0.005 to 0.18, z has a value ranging from 0.38 to 0.55 and k has a value ranging from 0.36 to 0.54.

In a first preferred embodiment y has a value ranging from 0.005 to 0.16, z has a value ranging from 0.39 to 0.55 and k has a value ranging from 0.37 to 0.54.

In a second preferred embodiment y has a value ranging from 0.011 to 0.16, z has a value ranging from 0.39 to 0.55 and k has a value ranging from 0.37 to 0.54.

In a third preferred embodiment y has a value ranging from 0.011 to 0.14, z has a value ranging from 0.40 to 0.55 and k has a value ranging from 0.38 to 0.54.

The values of y, z and k in the advantageous, first, second and third embodiments described above are obtained by using the ingredients ratios described respectively in the advantageous, first, second and third embodiments of the method described above.

All the conditions already cited above relating to the synthesis of the MeAPO apply to said other embodiment of the invention.

The Catalyst Composite May Also Comprise One or More Medium or Large Pore Molecular Sieves.

According to an embodiment of the invention, the catalyst composite may comprise a mixture of MeAPO molecular sieves and medium or large pore crystalline silicoaluminates, silicoaluminophosphates or mesoporous silicoaluminates. Among the products, which may be used for the molecular sieves of medium or large pore size, these include MFI, MEL, FER, MOR, FAU, BEA, AEL, AFI, LTL, MAZ, MWW and MCM-41. Preferably, they have pore apertures defined by ring sizes of 10 or more, preferably up to 12 tetrahedric atoms. More preferably, they have pore apertures defined by ring sizes of 10 or more, preferably up to 12 tetrahedric atoms and 10 or 12 oxygen atoms. Even more preferably, they have pore sizes greater than 0.5 nm. Most preferably they are of the MFI (ZSM-5 or silicalite), FAU, MOR, MEL or FER type. Zeolites may be pretreated by various ways, modified by P, by alkali, alkali-earth and/or rare-earth metals. Pretreatment may be carried out by acid leaching, steaming or combination thereof.

Advantageously (A) is a crystalline silicate of the MFI family which may be a zeolite, a silicalite or any other silicate in that family or the MEL family which may be a zeolite or any other silicate in that family. Examples of MFI silicates are ZSM-5 and silicalite. An example of an MEL zeolite is ZSM-11 which is known in the art. Other examples are Boralite D and silicalite-2 as described by the International Zeolite Association (*Atlas of Zeolite Structure Types,* 1987, Butterworths). Preferably, the medium or large pore molecular sieve is one or more of ZSM-5, a silicalite, a ferrierite, a P-ZSM-5, a P-silicalite, or a P-ferrierite.

Crystalline silicates are microporous crystalline inorganic polymers based on a framework of $XO_4$ tetrahydra linked to each other by sharing of oxygen ions, where X may be trivalent (e.g. Al, B, . . . ) or tetravalent (e.g. Ge, Si, . . . ). The crystal structure of a crystalline silicate is defined by the specific order in which a network of tetrahedral units are linked together. The size of the crystalline silicate pore openings is determined by the number of tetrahedral units, or, alternatively, oxygen atoms, required to form the pores and the nature of the cations that are present in the pores. They possess a unique combination of the following properties: high internal surface area; uniform pores with one or more discrete sizes; ion exchangeability; good thermal stability; and ability to adsorb organic compounds. Since the pores of these crystalline silicates are similar in size to many organic molecules of practical interest, they control the ingress and egress of reactants and products, resulting in particular selectivity in catalytic reactions. Crystalline silicates with the MFI structure possess a bi-directional intersecting pore system with the following pore diameters: a straight channel along [010]: 0.53-0.56 nm and a sinusoidal channel along [100]: 0.51-0.55 nm. Crystalline silicates with the MEL structure possess a bi-directional intersecting straight pore system with straight channels along [100] having pore diameters of 0.53-0.54 nm.

The MFI or MEL catalyst having a high silicon/aluminum atomic ratio may be manufactured by removing aluminum from a commercially available crystalline silicate. A typical commercially available silicalite has a silicon/aluminum atomic ratio of around 120 to 300. The commercially available MFI crystalline silicate may be modified by a steaming process which reduces the tetrahedral aluminum in the crystalline silicate framework and converts the aluminum atoms into octahedral aluminum in the form of amorphous alumina.

Although in the steaming step aluminum atoms are chemically removed from the crystalline silicate framework structure to form alumina particles, those particles cause partial obstruction of the pores or channels in the framework. Accordingly, following the steaming step, the crystalline silicate is subjected to an extraction step wherein amorphous alumina is removed from the pores and the micropore volume is, at least partially, recovered. The physical removal, by a leaching step, of the amorphous alumina from the pores by the formation of a water-soluble aluminum complex yields the overall effect of de-alumination of the MFI crystalline silicate. In this way by removing aluminum from the MFI crystalline silicate framework and then removing alumina formed therefrom from the pores, the process aims at achieving a substantially homogeneous de-alumination throughout the whole pore surfaces of the catalyst. This reduces the acidity of the catalyst and thereby reduces the occurrence of hydrogen transfer reactions in the cracking process. The framework silicon/aluminum ratio may be increased by this process to a value of at least about 180, preferably from about 180 to 1000, more preferably at least 200, yet more preferably at least 300 and most preferably around 480.

Regarding the mixture of the medium/large pore molecular sieve and MeAPO, if used, it can be made by co-synthesis procedure (synthesis of MeAPO-(A) composites materials) optionally followed by formulation into a catalyst. In another embodiment it can be formulated into a catalyst by combining with other materials that provide additional hardness or catalytic activity to the finished catalyst product. Materials, which can be blended with the mixture of medium/large pore molecular sieve and MeAPO can be various inert or catalytically active materials, or various binder materials. These materials include compositions such as kaolin and other clays, various forms of rare earth metals, alumina or alumina sol, titania, zirconia, quartz, silica or silica sol, and mixtures thereof. These components are effective in densifying the catalyst and increasing the strength of the formulated catalyst. The catalyst may be formulated into pellets, spheres, extruded into other shapes, or formed into a spray-dried powder.

The mixture of the medium/large pore molecular sieve and MeAPO can also be made by co-formulation procedure (blending of the separately synthesized medium/large pore molecular sieve and MeAPO) optionally followed by combination with a binder. This mixture of medium/large pore molecular sieve and MeAPO can be used as itself as a catalyst. In another embodiment it can be formulated into a catalyst by combining with other materials that provide additional hardness or catalytic activity to the finished catalyst product. The details are the same as above.

The mixture of the medium/large pore molecular sieve and MeAPO can also be made by blending of MeAPO and the medium/large pore molecular sieve, wherein at least one of the two components has been combined with a binder prior to the blending. The obtained mixture can be used as itself as a catalyst. In another embodiment it can be formulated into a catalyst by combining with other materials that provide additional hardness or catalytic activity to the finished catalyst product. The details are the same as above.

Preferably, the molecular sieves combination is a combination of SAPO-34, SAPO-44 or SAPO-18 with a ZSM-5, a silicalite, a ferrierite or a P-ZSM-5, a P-silicalite, a P-ferrierite.

The presence of the medium and large pore molecular sieve is optional. Advantageously, the molecular sieves comprise 70 to 99.9% by weight of the MeAPO molecular sieve and 0.01 to 30% by weight of the medium or large pore molecular sieve. More advantageously, the molecular sieves comprise 75 to 99.5% by weight of the MeAPO molecular sieve and 0.5 to 25% by weight of the medium or large pore molecular sieve. Most advantageously, the molecular sieves comprise 85 to 99% by weight of the MeAPO molecular sieve and 1 to 15% by weight of the medium or large pore molecular sieve.

According to an embodiment, the molecular sieves consist essentially of the MeAPO molecular sieve.

Regarding the metal salt, the catalyst composite further comprises at least 0.5% by weight of a metal salt, which, advantageously, contains a polyvalent metal or a metal possessing a large hydration diameter. More preferably, the content of metal salt in the catalyst composite ranges from 0.5 up to 95% by weight of the composite, more preferably 5 to 80% by weight. Preferably, the metal in the metal salt is selected from Ga, Al, Cs, Sr, Mg, Ca, Ba, Sc, Sn, Li, Co, Zn, more preferably from among Zn, Co, Ca, Mg. Without wishing to be bound by theory, the ion exchange reaction with these ions is very slow. For example, calcium must lose many of the strongly coordinated water molecules in order to enter the structure. Therefore, most of these ions cannot penetrate inside of the micropores and selectively poison the external surface. The specificity of the catalyst can thereby be better controlled.

The metal salt composition comprises at least one inorganic anion selected preferably from the group of silicates, borates and borosilicates. Suitable silicate anions include $SiO_3^{2-}$, $SiO_4^{4-}$, $Si_2O_7^{6-}$ and so on. Suitable borate anions include $BO_2^-$, $BO_3^{2-}$, $B_2O_5^{4-}$, $B_4O_7^{2-}$, $B_6O_{11}^{4-}$, $B_{10}O_{19}^{8-}$ and so on.

Bi-, tri- and poly-metal silicates, borates and borosilicates containing one, two or more metals selected from the list above can be used too.

The metal salt may also comprise other anions besides silicate, borates and borosilicates.

In an embodiment of the invention, a mixture of metal borates and metal silicates can be used.

The metal salt according to the invention are stable under the XTO conditions of the reactor i.e. at a temperature of 200 to 700° C. and at a pressure of 5 kPa to 5 MPa, thus acting as a catalyst promoter. "Stable" refers to the fact that the elements constituting the metal salt and having a positive valence remain part of the catalyst under pre-treatment conditions, XTO and regeneration conditions. This means that unlike metal oxides, the metal salts can be dehydrated, they may change morphology and even change colour under the conditions of the XTO reactor, yet the inorganic anion would still be essentially present as such. Furthermore, without wishing to be bound by theory, it is thought that the presence of one or more of silicate, borate and borosilicate anions further improves the catalytic properties of the catalyst composite.

Examples of suitable metal salt promoters include $Mg_2B_2O_5.H_2O$, $CaMgB_6O_{11}.6H_2O$ (hydroboracite), $Ca_2B_6O_{11}.5H_2O$ (colemanite), $Ca_4B_{10}O_{19}.7H_2O$, $Mg(BO_2).8H_2O$, $Ca(BO_2).2H_2O$, $BaB_6O_{10}.4H_2O$, $CaSi_6O_{17}(OH)_2$ (Xonotlite), $CaMg(Si_2O_6)_x$, $Mg_2(Si_2O_6)_x$, $CaAl_2Si_2O_8$ and mixtures thereof.

The preferred catalyst promoter is a calcium silicate with a very open and accessible pore structure. An even more preferred catalyst promoter comprises a synthetic crystalline hydrated calcium silicate having a chemical composition of $Ca_6Si_6O_{17}(OH)_2$ which corresponds to the known mineral xonotlite (having a molecular formula $6CaO.6SiO_2.H_2O$).

Generally, a synthetic hydrated calcium silicate is synthesised hydrothermally under autogenous pressure. A particularly preferred synthetic hydrated calcium silicate is available in commerce from the company Promat of Ratingen in Germany under the trade name Promaxon.

In order to demonstrate the thermal stability of xonotlite, and therefore the applicability of xonotlite as a catalyst promoter in MTO processes, commercial xonotlite sold under the trade name Promaxon D was calcined in ambient air at a relative humidity of about 50% at 650° C. for a period of 24 hours. The initial xonotlite had a crystalline phase $Ca_6Si_6O_{17}$(OH)$_2$ with a BET surface area of 51 m$^2$/gram and a pore volume (of less than 100 nanometers) of 0.35 ml/gram. After calcination at 650° C., the carrier retained its crystallinity, which corresponds to that of xonotlite. Thus after a 24 hour calcination at 650° C., the crystalline phase still comprised xonotlite ($Ca_6Si_6O_{17}$(OH)$_2$) with a BET surface area of 47.4 m$^2$/gram and a pore volume (less than 100 nanometers) of 0.30 ml/gram.

Before mixing with the molecular sieve said metal salt may be modified by calcination, steaming, ion-exchange, impregnation, or phosphatation. Said metal salt may be an individual compound or may be a part of mixed compounds, for example mixed with mineral, natural or chemical fertilizer.

The Metal Salt and Molecular Sieve(s) are Blended Together to Form the Catalyst Composite of the Invention.

The metal salt can be brought into contact with the molecular sieve by a co-formulation procedure or in situ blending in the reaction medium prior to the XTO process. Said contact can be realised by mechanically blending the molecular sieves with the metal salt. This can be carried out via any known blending method. Blending can last for a period of time starting from 1 minute up to 24 hours, preferably from 1 min to 10 hours. If not carried out in the XTO reactor in situ, it can be carried out in a batchwise mixer or in a continuous process, such as in an extruder e.g. a single or twin screw extruder at a temperature of from 20 to 300° C. under vacuum or elevated pressure. Said contact may be performed in an aqueous or non-aqueous medium. Prior to the formulation step, other compounds that aid the formulation may be added, like thickening agents or polyelectrolytes that improve the cohesion, dispersion and flowing properties of the precursor. In case of extrusion, rotating granulation or pelletising a rather dry (low water content) paste-like precursor is prepared. In case of oil-drop or spray-drying a rather liquid (high water content) is prepared. In another embodiment, the contact is carried out in the presence of phosphorus containing compounds. In a particular embodiment, the contact is carried out in the aqueous medium, preferably at a pH lower than 5, more preferably lower than 3.

Either prior to, after or simultaneously with the formulation step to form the composite, other components may be optionally blended with the molecular sieve. In a particular embodiment, the molecular sieve can be combined with other materials that provide additional hardness or catalytic activity to the finished catalyst product. Materials, which can be blended with the molecular sieve, can be various inert or catalytically active matrix materials and/or various binder materials. Such materials include clays, silica and/or metal oxides such as alumina. The latter is either naturally occurring or in the form of gelatinous precipitates or gels including mixtures of silica and metal oxides. In an embodiment, some binder materials can also serve as diluents in order to control the rate of conversion from feed to products and consequently improve selectivity. According to one embodiment, the binders also improve the crush strength of the catalyst under industrial operating conditions.

Naturally occurring clays, which can be used as binder, are for example clays from the kaolin family or montmorillonite family. Such clays can be used in the raw state as mined or they can be subjected to various treatments before use, such as calcination, acid treatment or chemical modification.

In addition to the foregoing, other materials, which can be included in the catalyst composite of the invention, include various forms of metal phosphates and sulphates (wherein the metal is chosen from one or more of Ca, Ga, Al, Ca, Ce, In, Cs, Sr, Mg, Ba, Sc, Sn, Li, Zn, Co, Mo, Mn, Ni, Fe, Cu, Cr, Ti and V), alumina or alumina sol, titania, zirconia, quartz, silica or silica sol, and mixtures thereof. Examples of possible phospates include amorphous calcium phosphate, monocalcium phosphate, dicalcium phosphate, dicalcium phosphate dehydrate, α- or β-tricalcium phosphate, octacalcium phosphate, hydroxyapatite etc.

Examples of possibly binary oxide binder compositions include, silica-alumina, silica magnesia, silica-zirconia, silica-thoria, silica-beryllia, silica-titania, calcium-alumina. Examples of ternary binder compositions include for instance calcium-silica-alumina or silica-alumina-zirconia.

These components are effective in increasing the density of the catalyst and increasing the strength of the formulated catalyst. The catalyst may be formulated into pellets, spheres, extruded into other shapes, or formed into spray-dried particles. Generally, the size of the catalyst particles can vary from about 20 to 5,000,000 µm. In general pellets, spheres and extrudates are employed in fixed bed reactors and exhibit a particle size of from about 0.5 mm to 5 mm. In general spray-dried particles are used in fluidised bed reactors, which exhibit a particle size of from about 20 to 200 µm. In particular, spheres are employed in moving bed reactors, which exhibit a size from about 0.5 to 5 mm. Spheres can be made in rotating granulator or by oil-drop methods. The crystal size of the molecular sieve contained in the catalyst composite is preferably less than about 10 µm, more preferably less than about 5 µm and most preferably less than about 4 µm. The amount of molecular sieve, which is contained in the final catalyst composite ranges from 10 to 99.5% by weight of the total catalyst composite, preferably 20 to 80% by weight.

According to another embodiment, non-modified molecular sieves were first formulated with a binder and matrix materials and then modified with phosphorous and alkaline earth metal silicates.

According to a further particular embodiment, molecular sieves were optionally dealuminated and then modified with phosphorous during the formulation step.

Introduction of the alkaline earth metal silicate can be performed during the formulation step or on the formulated solid.

According to a preferred embodiment, molecular sieves were first optionally dealuminated and modified with phosphorous and then formulated. Introduction of the metal is performed simultaneously with the phosphorous modification step and/or on the already formulated catalyst.

After physically blending the two components together, the catalyst composite may undergo further treatments including further steaming, leaching, washing, drying, calcination, impregnations and ion exchanging steps. If a zeolite is present, it can be modified with phosphorus prior to or after the step of introducing the metal salt to the molecular sieve.

With regards to the XTO process, the catalyst composite comprising the molecular sieves and metal salt according to the invention is particularly suited for the catalytic conversion of oxygen-containing, halogenide-containing or sulphur-containing organic compounds to hydrocarbons. Accordingly, the present invention also relates to a method for making an olefin product from an oxygen-containing, halogenide-containing or sulphur-containing organic feedstock wherein said oxygen-containing, halogenide-containing or sulphur-containing organic feedstock is contacted with the above catalyst composite under conditions effective to convert the oxygen-containing, halogenide-containing or sulphur-containing organic feedstock to olefin products (the effluent of the XTO). Said effluent comprises light olefins and a heavy hydrocarbon fraction.

In this process a feedstock containing an oxygen-containing, halogenide-containing or sulphur-containing organic compound contacts the above described catalyst composite in a reaction zone of a reactor at conditions effective to produce light olefins, particularly ethylene and propylene. Typically, the oxygen-containing, halogenide-containing or sulphur-containing organic feedstock is contacted with the catalyst composite when the oxygen-containing, halogenide-containing or sulphur-containing organic compounds are in vapour phase. Alternately, the process may be carried out in a liquid or a mixed vapour/liquid phase. In this process, converting oxygen-containing, halogenide-containing or sulphur-containing organic compounds, olefins can generally be produced at a wide range of temperatures. An effective operating temperature range can be from about 200° C. to 700° C. At the lower end of the temperature range, the formation of the desired olefin products may become markedly slow. At the upper end of the temperature range, the process may not form an optimum amount of product. An operating temperature of at least 300° C., and up to 575° C. is preferred.

The pressure also may vary over a wide range. Preferred pressures are in the range of about 5 kPa to about 5 MPa, with the most preferred range being of from about 50 kPa to about 0.5 MPa. The foregoing pressures refer to the partial pressure of the oxygen-containing, halogenide-containing, sulphur-containing organic compounds and/or mixtures thereof.

The process can be carried out in any system using a variety of transport beds, although a fixed bed or moving bed system could be used. Advantageously a fluidized bed is used. It is particularly desirable to operate the reaction process at high space velocities. The process can be conducted in a single reaction zone or a number of reaction zones arranged in series or in parallel. Any standard commercial scale reactor system can be used, for example fixed bed, fluidised or moving bed systems. After a certain time on-stream the catalyst needs to be regenerated. This regeneration can be carried out in a separate reactor or in the same reactor. In case of a moving bed or fluidised bed reactor, a part of the catalyst is continuously or intermittently withdrawn from the conversion reactor and sent to a second reactor for regeneration. After the regeneration, the regenerated catalyst is continuously or intermittently sent back to the conversion reactor. In case of fixed bed reactor the reactor is taken off-line for regeneration. Generally this requires a second spare reactor that can take over the conversion into light olefins. After regeneration the fixed bed reactor is in stand-by until the spare reactor needs regeneration and the regenerated reactor takes over the conversion. Regeneration is carried out by injecting an oxygen-containing stream over the catalyst at sufficiently high temperature to burn the deposited coke on the catalyst. The commercial scale reactor systems can be operated at a weight hourly space velocity (WHSV) of from 0.1 hr$^{-1}$ to 1000 hr$^{-1}$.

One or more inert diluents may be present in the feedstock, for example, in an amount of from 1 to 95 molar percent, based on the total number of moles of all feed and diluent components fed to the reaction zone. Typical diluents include, but are not necessarily limited to helium, argon, nitrogen, carbon monoxide, carbon dioxide, hydrogen, water, paraffins, alkanes (especially methane, ethane, and propane), aromatic compounds, and mixtures thereof. The preferred diluents are water and nitrogen. Water can be injected in either liquid or vapour form.

The oxygenate feedstock is any feedstock containing a molecule or any chemical having at least an oxygen atom and capable, in the presence of the above MeAPO catalyst composite, to be converted to olefin products. The oxygenate feedstock comprises at least one organic compound which contains at least one oxygen atom, such as aliphatic alcohols, ethers, carbonyl compounds (aldehydes, ketones, carboxylic acids, carbonates, esters and the like). Representative oxygenates include but are not necessarily limited to lower straight and branched chain aliphatic alcohols and their unsaturated counterparts. Examples of suitable oxygenate compounds include, but are not limited to: methanol; ethanol; n-propanol; isopropanol; $C_4$-$C_{20}$ alcohols; methyl ethyl ether; dimethyl ether; diethyl ether; di-isopropyl ether; formaldehyde; dimethyl carbonate; dimethyl ketone; acetic acid; and mixtures thereof. Representative oxygenates include lower straight chain or branched aliphatic alcohols, their unsaturated counterparts. Analogously to these oxygenates, compounds containing sulphur or halides may be used. Examples of suitable compounds include methyl mercaptan; dimethyl sulfide; ethyl mercaptan; di-ethyl sulfide; ethyl monochloride; methyl monochloride, methyl dichloride, n-alkyl halides, n-alkyl sulfides having n-alkyl groups of comprising the range of from about 1 to about 10 carbon atoms; and mixtures thereof. Preferred oxygenate compounds are methanol, dimethyl ether, or a mixture thereof.

In XTO effluent among the olefins having 4 carbon atoms or more there are 50 to 85 weight % of butenes. More than 85% by weight and advantageously more than 95% of the hydrocarbons having 4 carbon atoms or more are C4 to C8 olefins.

According to an advantageous embodiment of the invention said olefin products (the effluent of the XTO) are fractionated to form a stream comprising essentially ethylene and at least a part of said stream is recycled on the catalyst composite to increase the propylene production and then the flexibility of ethylene vs propylene production. Advantageously the ratio of ethylene to the oxygen-containing, halogenide-containing or sulphur-containing organic feedstock is 1.8 or less.

The present invention also relates to a process (hereunder referred to as the "combined XTO and OCP process") to make light olefins from an oxygen-containing, halogenide-containing or sulphur-containing organic feedstock comprising:

contacting said oxygen-containing, halogenide-containing or sulphur-containing organic feedstock in the MTO reactor with the above catalyst at conditions effective to convert at least a portion of the feedstock to form an MTO reactor effluent comprising light olefins and a heavy hydrocarbon fraction;

separating said light olefins from said heavy hydrocarbon fraction;

contacting said heavy hydrocarbon fraction in the OCP reactor at conditions effective to convert at least a portion of said heavy hydrocarbon fraction to light olefins.

The effluent of the XTO reactor comprising light olefins and a heavy hydrocarbon fraction is sent to a fractionation section to separate said light olefins from said heavy hydrocarbon fraction. With regards to said effluent of the XTO process, "light olefins" means ethylene and propylene and the "heavy hydrocarbon fraction" is defined herein as the fraction containing hydrocarbons having a molecular weight greater than propane, which means hydrocarbons having 4 carbon atoms or more and written as $C_4^+$. It is desirable to have a substantially 100% conversion of the organic compound in the primary reactor. This conversion rate is adjusted by optimization of contact time and the frequency of regeneration of the catalyst.

With regards to the OCP process, said process is known per se. It has been described in EP 1036133, EP 1035915, EP 1036134, EP 1036135, EP 1036136, EP 1036138, EP 1036137, EP 1036139, EP 1194502, EP 1190015, EP 1194500 and EP 1363983 the content of which are incorporated in the present invention.

The heavy hydrocarbon fraction produced in the XTO reactor is converted in the OCP reactor, also called an "olefin cracking reactor" herein, to produce additional amounts of ethylene and propylene. Advantageously the catalysts found to produce this conversion comprise a crystalline silicate of the MFI family, which may be a zeolite, a silicalite or any other silicate in that family, or of the MEL family, which may be a zeolite or any other silicate in that family. These catalysts have been described above in the description of the medium and large pore molecular sieves suitable for the invention.

The crystalline silicate catalyst has structural and chemical properties and is employed under particular reaction conditions whereby the catalytic cracking of the $C_4^+$ olefins readily proceeds. Different reaction pathways can occur on the catalyst. Under the process conditions, having an inlet temperature of around 400° to 600° C., preferably from 520° to 600° C., yet more preferably 540° to 580° C., and an olefin partial pressure of from 0.1 to 2 bars, most preferably around atmospheric pressure. Olefinic catalytic cracking may be understood to comprise a process yielding shorter molecules via bond breakage. With such high silicon/aluminum ratio in the crystalline silicate catalyst, a stable olefin conversion can be achieved with a high propylene yield on an olefin basis.

The MFI catalyst having a high silicon/aluminum atomic ratio for use in the OCP reactor of the present invention may be manufactured by removing aluminum from a commercially available crystalline silicate. A typical commercially available silicalite has a silicon/aluminum atomic ratio of around 120. The commercially available MFI crystalline silicate may be modified by a steaming process, which reduces the tetrahedral aluminum in the crystalline silicate framework and converts the aluminum atoms into octahedral aluminum in the form of amorphous alumina. Although in the steaming step aluminum atoms are chemically removed from the crystalline silicate framework structure to form alumina particles, those particles cause partial obstruction of the pores or channels in the framework. This inhibits the olefin cracking processes of the present invention. Accordingly, following the steaming step, the crystalline silicate is subjected to an extraction step wherein amorphous alumina is removed from the pores and the micropore volume is, at least partially, recovered. The physical removal, by a leaching step, of the amorphous alumina from the pores by the formation of a water-soluble aluminum complex yields the overall effect of de-alumination of the MFI crystalline silicate. In this way by removing aluminum from the MFI crystalline silicate framework and then removing alumina formed there from the pores, the process aims at achieving a substantially homogeneous de-alumination throughout the whole pore surfaces of the catalyst. This reduces the acidity of the catalyst and thereby reduces the occurrence of hydrogen transfer reactions in the cracking process. The reduction of acidity ideally occurs substantially homogeneously throughout the pores defined in the crystalline silicate framework. This is because in the olefin-cracking process hydrocarbon species can enter deeply into the pores. Accordingly, the reduction of acidity and thus the reduction in hydrogen transfer reactions which would reduce the stability of the MFI catalyst are pursued throughout the whole pore structure in the framework. The framework silicon/aluminum ratio may be increased by this process to a value of at least about 180, preferably from about 180 to 1000, more preferably at least 200, yet more preferably at least 300 and most preferably around 480.

The MEL or MFI crystalline silicate catalyst may be mixed with a binder, preferably an inorganic binder, and shaped to a desired shape, e.g. extruded pellets. The binder is selected so as to be resistant to the temperature and other conditions employed in the catalyst manufacturing process and in the subsequent catalytic cracking process for the olefins. The binder is an inorganic material selected from clays, silica, metal oxides such as $ZrO_2$ and/or metals, or gels including mixtures of silica and metal oxides. The binder is preferably alumina-free, although aluminum in certain chemical compounds as in aluminium phosphates ($AlPO_4$) may be used as the latter are quite inert and not acidic in nature. If the binder which is used in conjunction with the crystalline silicate is itself catalytically active, this may alter the conversion and/or the selectivity of the catalyst. Inactive materials for the binder may suitably serve as diluents to control the amount of conversion so that products can be obtained economically and orderly without employing other means for controlling the reaction rate. It is desirable to provide a catalyst having a good crush strength. This is because in commercial use, it is desirable to prevent the catalyst from breaking down into powder-like materials. Such clay or oxide binders have been employed normally only for the purpose of improving the crush strength of the catalyst. A particularly preferred binder for the catalyst of the present invention comprises silica or $AlPO_4$.

The relative proportions of the finely divided crystalline silicate material and the inorganic oxide matrix of the binder can vary widely. Typically, the binder content ranges from 5 to 95% by weight, more typically from 20 to 50% by weight, based on the weight of the composite catalyst. Such a mixture of crystalline silicate and an inorganic oxide binder is referred to as a formulated crystalline silicate.

In mixing the catalyst with a binder, the catalyst may be formulated into pellets, spheres, extruded into other shapes, or formed into a spray-dried powder. In the catalytic cracking process of the OCP reactor, the process conditions are selected in order to provide high selectivity towards propylene or ethylene, as desired, a stable olefin conversion over time, and a stable olefinic product distribution in the effluent. Such objectives are favoured by the use of a low acid density in the catalyst (i.e. a high Si/Al atomic ratio) in conjunction with a low pressure, a high inlet temperature and a short contact time, all of which process parameters are interrelated and provide an overall cumulative effect. The process conditions are selected to disfavour hydrogen transfer reactions leading to the formation of paraffins, aromatics and coke precursors. The process operating conditions thus employ a high space velocity, a low pressure and a high reaction temperature. The LHSV ranges from 5 to 30 $hr^{-1}$, preferably from 10 to 30 $hr^{-1}$. The olefin partial pressure ranges from 0.1 to 2 bars, preferably from 0.5 to 1.5 bars (absolute pressures referred to herein). A particularly preferred olefin partial pressure is atmospheric pressure (i.e. 1 bar). The heavy hydrocarbon fraction feedstock is preferably fed at a total inlet pressure sufficient to convey the feedstocks through the reactor. Said feedstock may be fed undiluted or diluted in an inert gas, e.g. nitrogen or steam. Preferably, the total absolute pressure in the second reactor ranges from 0.5 to 10 bars. The use of a low olefin partial pressure, for example atmospheric pressure, tends to lower the incidence of hydrogen transfer reactions in the cracking process, which in turn reduces the potential for coke formation, which tends to reduce catalyst stability. The cracking of the olefins is preferably performed at an inlet temperature of the feedstock of from 400° to 650° C., more preferably from 450° to 600° C., yet more preferably from 540° C. to 590° C., typically around 560° to 585° C.

In order to maximize the amount of ethylene and propylene and to minimize the production of methane, aromatics and coke, it is desired to minimize the presence of diolefins in the feed. Diolefin conversion to monoolefin hydrocarbons may be accomplished with a conventional selective hydrogenation process such as disclosed in U.S. Pat. No. 4,695,560 hereby incorporated by reference.

The OCP reactor can be a fixed bed reactor, a moving bed reactor or a fluidized bed reactor. A typical fluid bed reactor is one of the FCC type used for fluidized-bed catalytic cracking in the oil refinery. A typical moving bed reactor is of the continuous catalytic reforming type. As described above, the process may be performed continuously using a pair of parallel "swing" reactors. The heavy hydrocarbon fraction cracking process is endothermic; therefore, the reactor should be adapted to supply heat as necessary to maintain a suitable reaction temperature. Online or periodic regeneration of the catalyst may be provided by any suitable means known in the art.

The various preferred catalysts of the OCP reactor have been found to exhibit high stability, in particular being capable of giving a stable propylene yield over several days, e.g. up to ten days. This enables the olefin cracking process to be performed continuously in two parallel "swing" reactors wherein when one reactor is operating, the other reactor is undergoing catalyst regeneration. The catalyst can be regenerated several times.

The OCP reactor effluent comprises methane, light olefins and hydrocarbons having 4 carbon atoms or more. Advantageously said OCP reactor effluent is sent to a fractionator and the light olefins are recovered. Advantageously the hydrocarbons having 4 carbon atoms or more are recycled at the inlet of the OCP reactor, optionally mixed with the heavy hydrocarbon recovered from the effluent of the XTO reactor. Advantageously, before recycling said hydrocarbons having 4 carbon atoms or more at the inlet of the OCP reactor, said hydrocarbons having 4 carbon atoms or more are sent to a second fractionator to purge the heavies. In a preferred embodiment the light olefins recovered from the effluent of the XTO reactor and the light olefins recovered from the fractionator following the OCP reactor are treated in a common recovery section.

Optionally, in order to adjust the propylene to ethylene ratio of the whole process (XTO+OCP), ethylene in whole or in part can be recycled over the OCP reactor and advantageously converted into more propylene. This ethylene can either come from the fractionation section of the XTO reactor or from the fractionation section of the OCP reactor or from both the fractionation section of the XTO reactor and the fraction section of the OCP reactor or even from the optional common recovery section.

Optionally, in order to adjust the propylene to ethylene ratio of the whole process (XTO+OCP), ethylene in whole or in part can be recycled over the XTO reactor where it combines with the oxygen-containing, halogenide-containing or sulphur-containing organic feedstock to form more propylene. This ethylene can either come from the fractionation section of the XTO reactor or from the fractionation section of the OCP reactor or from both the fractionation section of the XTO reactor and the fraction section of the OCP reactor or even from the optional common recovery section.

These ways of operation allow to respond with the same equipment and catalyst to market propylene to ethylene demand.

The performance of the catalyst of the present invention is substantially better than the simple sum of the individual components. This shows a synergy of at least one molecular sieve in the XTO and a metal salt to produce very particular catalytic properties. The catalyst composite shows good behaviour in XTO processes in terms of stability and C3/C2 ratio, propylene purity and heavy olefins production (higher C4+ olefin yield for recycling).

FIG. 1 illustrates a specific embodiment of the invention. The effluent of the XTO reactor is passed to a fractionator 11. The overhead, a C1-C3 fraction including the light olefins is sent via line 2 to a common recovery section (not shown). The bottoms (the heavy hydrocarbon fraction) are sent via line 3 to the OCP reactor. The effluent of the OCP reactor is sent via line 10 to a fractionator 8. The overhead, a C1-C3 fraction including the light olefins, is sent via line 9 to a common recovery section (not shown). The bottoms, hydrocarbons having 4 carbon atoms or more, are sent to a fractionator 5. The overhead, hydrocarbons having 4 to substantially 5 carbon atoms are recycled via line 4 at the inlet of the OCP reactor. The bottoms, hydrocarbons having substantially 6 carbon atoms or more, are purged via line 6.

The method of making the olefin products from an oxygenate feedstock can include the additional step of making the oxygenate feedstock from hydrocarbons such as oil, coal, tar sand, shale, biomass and natural gas. Methods for making oxygenate feedstocks are known in the art. These methods include fermentation to alcohol or ether, making synthesis gas, then converting the synthesis gas to alcohol or ether. Synthesis gas can be produced by known processes such as steam reforming, autothermal reforming and partial oxidization in case of gas feedstocks or by reforming or gasification using oxygen and steam in case of solid (coal, organic waste) or liquid feedstocks. Methanol, methylsulfide and methylhalides can be produced by oxidation of methane with the help of dioxygen, sulphur or halides in the corresponding oxygen-containing, halogenide-containing or sulphur-containing organic compound.

One skilled in the art will also appreciate that the olefin products made by the oxygenate-to-olefin conversion reaction using the molecular sieve of the present invention can be polymerized to form polyolefins, particularly polyethylenes and polypropylenes. The present invention relates also to said polyethylenes and polypropylenes.

EXAMPLES

Example 1

A sample of SAPO-34 from UOP was obtained through "Customec". This sample showed a silicon content (Si/(Si+Al+P)) of 0.41 and represents a cubic crystal morphology with an average size of 0.4 µm.

The sample is hereinafter identified as Comparative I.

Example 2

A sample identified hereinafter as Sample A was prepared by mechanically blending 80 wt % of the solid described in example I with 20 wt % of xonotlite $CaSi_6O_{17}(OH)_2$.

Example 3

Catalyst tests were performed on 2 g catalyst samples with an essentially pure methanol feed at 450° C., at a pressure of 0.5 barg and WHSV=1.6 h$^{-1}$, in a fixed-bed, down-flow stainless-steel reactor. Catalyst powder was pressed into wafers and crushed to 35-45 mesh particles. Prior to catalytic run all catalysts were heated in flowing $N_2$ (5 Nl/h) up to the reaction temperature. Analysis of the products has been performed on-line by a gas chromatograph equipped with a capillary column. Catalytic performances of MeAPOs molecular sieves were compared at 100% methanol conversion and maximum catalyst activity just before appearance of DME in the effluent. The results are provided in Table I. The values regarding the composition of the effluent from the MTO reactor are the weight percent on a carbon basis and water-free.

TABLE I

|  | Comparative I SAPO-34 100 wt % | Sample A SAPO-34 + xonotlite 80 wt % + 20 wt % |
|---|---|---|
| T/° C. | 450 | 450 |
| WHSV/h$^{-1}$ | 1.6 | 1.6 |
| P/barg | 0.5 | 0.5 |
| C1 | 5.4 | 3.9 |
| Paraffins | 8.4 | 5.8 |
| Olefins | 90.7 | 92.7 |
| Aromatics | 0.3 | 0.3 |
| Purity C3's | 97.8 | 99.4 |
| C3/C2 | 0.7 | 0.7 |
| C2 + C3 | 77.6 | 81.4 |
| ethylene | 44.8 | 46.7 |
| propylene | 32.7 | 34.7 |

The invention claimed is:

1. A catalyst composite comprising:
   at least 0.5% by weight of at least one metal salt, which is stable under temperatures of 200 to 700° C. and pressures of 5 to 5000 kPa, wherein the metal salt is selected from the group consisting of $Mg_2B_2O_5.H_2O$, $CaMgB_6O_{11}.6H_2O$ (hydroboracite), $Ca_2B_6O_{11}.5H_2O$ (colemanite), $Ca_4B_{10}O_{19}.7H_2O$, $Mg(BO_2).8H_2O$, $Ca(BO_2).2H_2O$, $BaB_6O_{10}.4H_2O$, $CaSi_6O_{17}(OH)_2$ (xonotlite), $CaMg(Si_2O_6)x$, $Mg_2(Si_2O_6)x$, $CaAl_2Si_2O_8$ and combinations thereof;
   at least 10% by weight of molecular sieves which comprise 70 to 100% by weight of molecular sieves of at least one small pore aluminosilicate or small pore metalloaluminophosphate (MeAPO) molecular sieve and 0 to 30% by weight of molecular sieves of at least one medium or large pore molecular sieve comprising pore apertures defined by ring sizes of at least 10 tetrahedric atoms;
   wherein the at least one small pore aluminosilicate or small pore MeAPO molecular sieve comprises pore apertures defined by ring sizes of up to 8 tetrahedric atoms;
   wherein the at least one medium or large pore molecular sieve is selected from the group consisting of crystalline silicoaluminates, silicoaluminophosphates, mesoporous silicoaluminates and combinations thereof;
   wherein the MeAPO molecular sieve has predominantly a plate crystal morphology in which the width (W) and the thickness (T) are represented by the formula:

$W/T \geq 10$.

2. The catalyst composite of claim 1, wherein the catalyst composite comprises from 0.5% to 10% by weight of the at least one metal salt.

3. A catalyst composite comprising:
   at least 0.5% by weight of at least one metal salt, which is stable under temperatures of 200 to 700° C. and pressures of 5 to 5000 kPa, wherein the metal salt is $CaSi_6O_{17}(OH)_2$ (xonotlite);
   at least 10% by weight of molecular sieves which comprise 70 to 100% by weight of molecular sieves of at least one small pore aluminosilicate or small pore metalloaluminophosphate (MeAPO) molecular sieve and 0 to 30% by weight of molecular sieves of at least one medium or large pore molecular sieve comprising pore apertures defined by ring sizes of at least 10 tetrahedric atoms;
   wherein the at least one small pore aluminosilicate or small pore MeAPO molecular sieve comprises pore apertures defined by ring sizes of up to 8 tetrahedric atoms;
   wherein the at least one medium or large pore molecular sieve is selected from the group consisting of crystalline silicoaluminates, silicoaluminophosphates, mesoporous silicoaluminates and combinations thereof;
   wherein the MeAPO molecular sieve has predominantly a plate crystal morphology in which the width (W) and the thickness (T) are represented by the formula:

$W/T \geq 10$.

4. The catalyst composite of claim 1, wherein the molecular sieves comprise 70 to 99.9% by weight of the MeAPO molecular sieve and 0.01 to 30% by weight of the medium or large pore molecular sieve.

5. The catalyst composite of claim 1, wherein the molecular sieves comprise 75 to 99.5% by weight of the MeAPO molecular sieve and 0.5 to 25% by weight of the medium or large pore molecular sieve.

6. The catalyst composite of claim 1, wherein the medium pore crystalline silicoaluminate molecular sieves are selected from the group consisting of MFI, FER, MEL and combinations thereof.

7. The catalyst composite of claim 1, wherein the medium pore crystalline silicoaluminate molecular sieve is selected from the group consisting of ZSM-5, silicalite, P-ferrierite and combinations thereof.

8. The catalyst composite of claim 1, wherein the medium pore silicoaluminophosphate material is AEL.

9. The catalyst composite of claim 1, wherein the large pore crystalline silicoaluminates are selected from the group consisting of FAU, MOR, LTL, MAZ, MWW, BEA and combinations thereof.

10. A catalyst composite comprising:
    at least 0.5% by weight of at least one metal salt, which is stable under temperatures of 200 to 700° C. and pressures of 5 to 5000 kPa, wherein the metal salt is selected from the group consisting of $Mg_2B_2O_5.H_2O$, $CaMgB_6O_{11}.6H_2O$ (hydroboracite), $Ca_2B_6O_{11}.5H_2O$ (colemanite), $Ca_4B_{10}O_{19}.7H_2O$, $Mg(BO_2).8H_2O$, $Ca(BO_2).2H_2O$, $BaB_6O_{10}.4H_2O$, $CaSi_6O_{17}(OH)_2$ (xonotlite), $CaMg(Si_2O_6)x$, $Mg_2(Si_2O_6)x$, $CaAl_2O_8$ and combinations thereof;
    at least 10% by weight of molecular sieves which comprise 70 to 100% by weight of molecular sieves of at least one small pore aluminosilicate or small pore metalloaluminophosphate (MeAPO) molecular sieve and 0 to 30% by weight of molecular sieves of at least one medium or large pore molecular sieve comprising pore apertures defined by ring sizes of at least 10 tetrahedric atoms;
    wherein the at least one small pore aluminosilicate or small pore MeAPO molecular sieve comprises pore apertures defined by ring sizes of up to 8 tetrahedric atoms;
    wherein the at least one medium or large pore molecular sieve is selected from the group consisting of crystalline silicoaluminates, silicoaluminophosphates, and mesoporous silicoaluminates and combinations thereof; and wherein the large pore silicoaluminophosphate materials is AFI.

11. A catalyst composite comprising:
   at least 0.5% by weight of at least one metal salt, which is stable under temperatures of 200 to 700° C. and pressures of 5 to 5000 kPa, wherein the metal salt is selected from the group consisting of $Mg_2B_2O_5.H_2O$, $CaMgB_6O_{11}.6H_2O$ (hydroboracite), $Ca_2B_6O_{11}.5H_2O$ (colemanite), $Ca_4B_{10}O_{19}.7H_2O$, $Mg(BO_2).8H_2O$, $Ca(BO_2).2H_2O$, $BaB_6O_{10}.4H_2O$, $CaSi_6O_{17}(OH)$, (xonotlite), $CaMg(Si_2O_6)x$, $Mg_2(Si_2O_6)x$, and $CaAl_2Si_2O_8$ and combinations thereof;
   at least 10% by weight of molecular sieves which comprise 70 to 100% by weight of molecular sieves of at least one small pore aluminosilicate or small pore metalloaluminophosphate (MeAPO) molecular sieve and 0 to 30% by weight of molecular sieves of at least one medium or large pore molecular sieve comprising pore apertures defined by ring sizes of at least 10 tetrahedric atoms;
   wherein the at least one small pore aluminosilicate or small pore MeAPO molecular sieve comprises pore apertures defined by ring sizes of up to 8 tetrahedric atoms;
   wherein the at least one medium or large pore molecular sieve is selected from the group consisting of crystalline silicoaluminates, silicoaluminophosphates, and mesoporous silicoaluminates and combinations thereof; and
   wherein the mesoporous silicoaluminate is MCM-41.

12. The catalyst composite of claim 1, wherein the MeAPO molecular sieves have essentially a structure CHA or AEI or a mixture thereof.

13. The catalyst composite of claim 1, wherein the MeAPO molecular sieves have essentially the structure SAPO-18, SAPO-34, SAPO-44, SAPO-17, SAPO-35 or a mixture thereof.

14. The catalyst composite of claim 1, wherein MeAPO is an intergrown phase of two MeAPO having AEI and CHA framework types.

15. The catalyst composite of claim 1, wherein the MeAPO molecular sieve has an empirical chemical composition on an anhydrous basis, after synthesis and calcination, expressed by the formula $H_xMe_yAl_zP_kO_2$, in which:
   y+z+k=1; and
   x is less than or equal to y, wherein:
   y has a value ranging from 0.0008 to 0.4,
   z has a value ranging from 0.25 to 0.67,
   k has a value ranging from 0.2 to 0.67.

16. The catalyst composite of claim 1, wherein W/T ranges from 10 to 100.

17. The catalyst composite of claim 1, wherein T ranges from 0.01 to 0.07 μm.

18. The catalyst composite of claim 16, wherein T ranges from 0.04 to 0.07 μm.

19. The catalyst composite of claim 1, wherein the MeAPO is prepared by a method comprising:
   forming a reaction mixture containing a texture influencing agent (TIA), an organic templating agent (TEMP), and a reactive source wherein the reactive source is a reactive inorganic source of $MeO_2$ essentially insoluble in the TIA, $Al_2O_3$, $P_2O_5$ or combinations thereof;
   crystallizing the above reaction mixture thus formed until crystals of the metalloaluminophosphate (MeAPO) are formed;
   recovering a solid reaction product; washing it with water to remove the TIA; and
   calcinating it to remove the organic template.

20. The catalyst composite of claim 1, wherein in the MeAPO, Me is a metal selected from the group consisting of Si, Ge, Mg, Zn, Fe, Co, Ni, Mn, Cr, Ca, Ba, Mo, Cu, Ga, Sn, Ti and mixtures thereof.

21. The catalyst composite of claim 20, wherein Me is Si.

22. The catalyst composite of claim 1, wherein a metal selected from the group consisting of Si, Mg, Zn, Ge, Fe, Co, Ni, Mn, Cr, Ca, Ba, Mo, Cu, Ga, Sn, Ti and mixtures thereof is added to the molecular sieve(s) before blending with the metal salt.

23. The catalyst composite of claim 1, wherein the composite further comprises metal phosphates and/or sulphates comprising at least one metal selected from the group consisting of Zn, Co, Ca, Mg, Ga, Al, Cs, Sr, Ba, Sc, Sn, and Li.

24. The catalyst composite of claim 1, wherein the metal salt is introduced to the molecular sieve(s) by one of the following two methods:
   during the formulation step of the catalyst by mechanically blending the molecular sieve with a metal silicate forming a precursor;
   or physical blending of the previously formulated molecular sieve and the previously formulated metal silicate in situ in an XTO and/or OCP reaction medium.

25. The catalyst composite of claim 24, wherein after introduction of the metal salt to the molecular sieves, the composite can be post-treated by calcinations, reduction steaming or P-modification of any zeolites.

26. A process for making an olefin product from an oxygen-containing, halogenide-containing or sulphur-containing organic feedstock wherein the oxygen-containing, halogenide-containing or sulphur-containing organic feedstock is contacted in an XTO reactor with the catalyst composite of claim 1 under conditions effective to convert the oxygen-containing, halogenide-containing or sulphur-containing organic feedstock to produce an XTO reactor effluent comprising a heavy hydrocarbon fraction and olefin products comprising ethylene and propylene.

27. The process of claim 26, wherein the XTO reactor effluent comprising light olefins and a heavy hydrocarbon fraction is sent to a fractionation section to separate said light olefins from the heavy hydrocarbon fraction and the heavy hydrocarbon fraction is recycled to the XTO reactor at conditions in the XTO reactor effective to convert at least a portion of the heavy hydrocarbon fraction to olefin products.

28. The process of claim 26, wherein the olefin products are fractionated to form a stream comprised essentially of ethylene and at least a part of said stream is recycled to the XTO reactor to increase the propylene production.

29. The process of claim 26, wherein the XTO reactor effluent comprising light olefins and a heavy hydrocarbon fraction is sent to a fractionation section to separate the light olefins from said heavy hydrocarbon fraction and the heavy hydrocarbon fraction is sent in an OCP reactor at conditions in the OCP reactor effective to convert at least a portion of the heavy hydrocarbon fraction to light olefins.

30. The process of claim 29, wherein the OCP reactor effluent is sent to a fractionator and the light olefins are recovered and hydrocarbons having 4 carbon atoms or more are recycled to an inlet of the OCP reactor, and mixed with the heavy hydrocarbon recovered from the effluent of the XTO reactor.

31. The process of claim 30, wherein before recycling the hydrocarbons having 4 carbon atoms or more to an inlet of the OCP reactor, the hydrocarbons having 4 carbon atoms or more are sent to a second fractionator to purge heavies.

32. The process of claim 29, wherein in order to adjust the propylene to ethylene ratio of the whole process, ethylene in whole or in part is recycled to the OCP reactor and the ethylene can either come from the fractionation section of the XTO reactor or from the fractionation section of the OCP reactor or from both the fractionation section of the XTO reactor and the fractionation section of the OCP reactor or from a common recovery section.

33. The process of claim 29, wherein in order to adjust the propylene to ethylene ratio of the whole process, ethylene in whole or in part is recycled to the XTO reactor and the ethylene can either come from the fractionation section of the XTO reactor or from the fractionation section of the OCP reactor or from both the fractionation section of the XTO reactor and the fraction section of the OCP reactor or from a common recovery section.

34. The process of claim 26, wherein ethylene is further polymerized with one or more comonomers.

35. The process of claim 26, wherein propylene is further polymerized with one or more comonomers.

* * * * *